United States Patent [19]

Kallassy

[11] Patent Number: 4,729,370

[45] Date of Patent: Mar. 8, 1988

[54] ANKLE SUPPORT

[76] Inventor: Charles Kallassy, 1933 Estrada Pkwy. #328, Irving, Tex. 75061

[21] Appl. No.: 861,515

[22] Filed: May 9, 1986

[51] Int. Cl.$^4$ ............................................. A61F 13/06
[52] U.S. Cl. .................................. 128/166; 128/80 H
[58] Field of Search ..................... 128/166, 165, 80 H, 128/80 R; 36/89, 90

[56] References Cited

U.S. PATENT DOCUMENTS

| | | | |
|---|---|---|---|
| 487,492 | 12/1892 | Pugsley | 128/166 |
| 3,073,305 | 1/1963 | Biggs, Jr. et al. | 128/166 |
| 3,490,450 | 1/1970 | Gardner | 128/166 |
| 4,367,733 | 1/1983 | Stromgren | 128/166 |
| 4,590,932 | 5/1986 | Wilkerson | 128/80 H X |

FOREIGN PATENT DOCUMENTS 183418  4/1907  Fed. Rep. of Germany ...... 128/166

Primary Examiner—Clifford D. Crowder
Attorney, Agent, or Firm—Darby & Darby

[57] ABSTRACT

An ankle support is provided with an underliner having multi-directional stretch which fits over the wearer's foot in the manner of a sock and extends to a point above the ankle. A non-stretch lateral strap is secured to the underliner at a point below the ankle joint and extends upwardly to the top of the underliner, where it is inelastically secured, with provision being made for adjustment of its tension. A non-stretch medial strap is inelastically connected to the lateral strap therebelow. The medial strap extends underneath the foot and up the opposite side thereof, and it is inelastically secured to the leg near the top of the underliner, with provision being made for adjustment of its tension. The medial strap thereby supports the wearer's arch and, in combination with the lateral strap, supports the ligaments of the ankle joint and provides a "heel lock", to limit and balance the lateral movement of the ankle joint.

25 Claims, 7 Drawing Figures

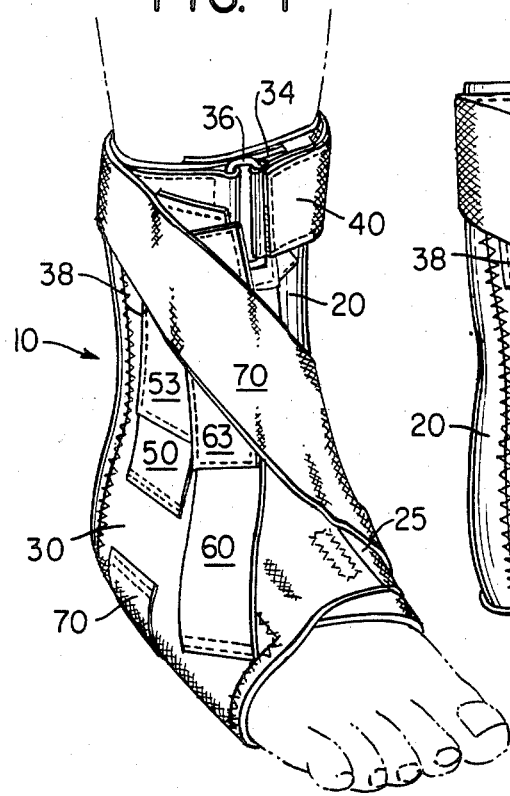
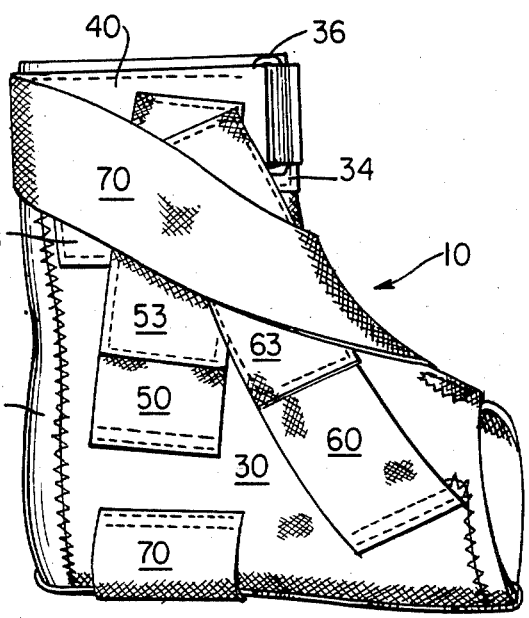
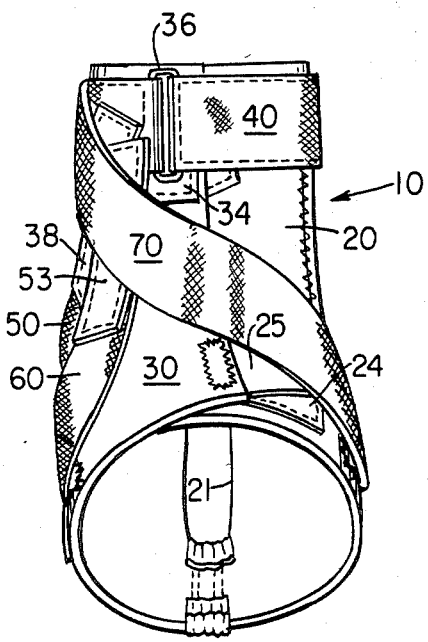
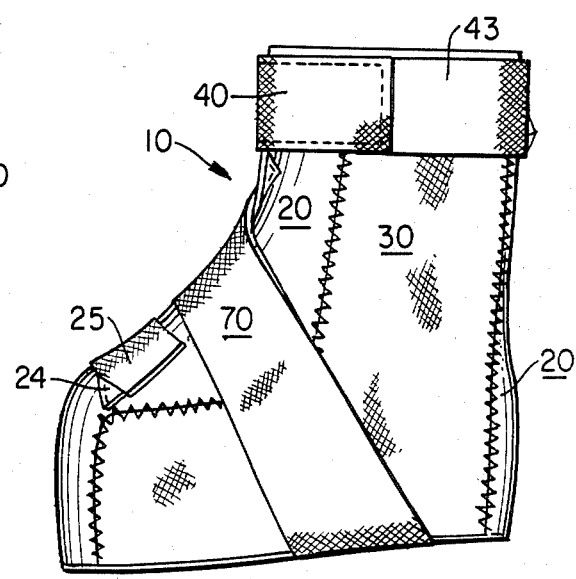

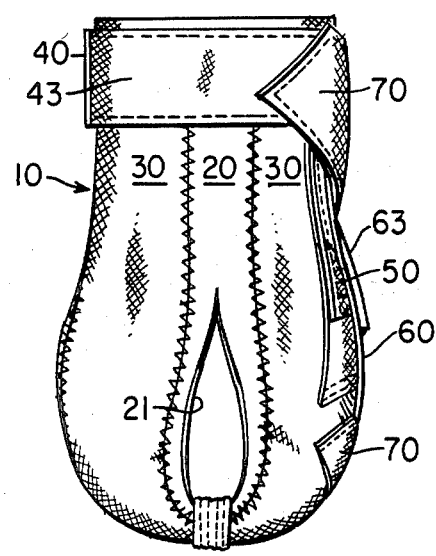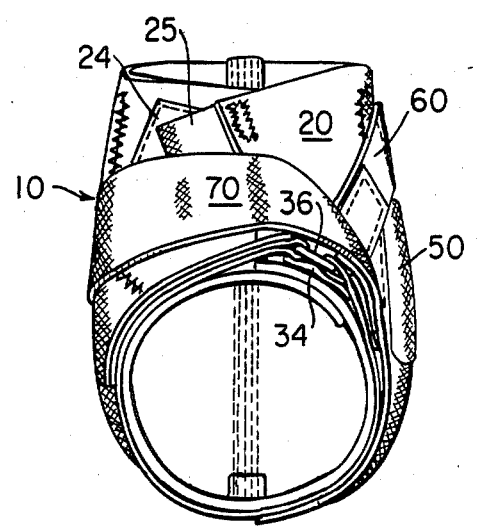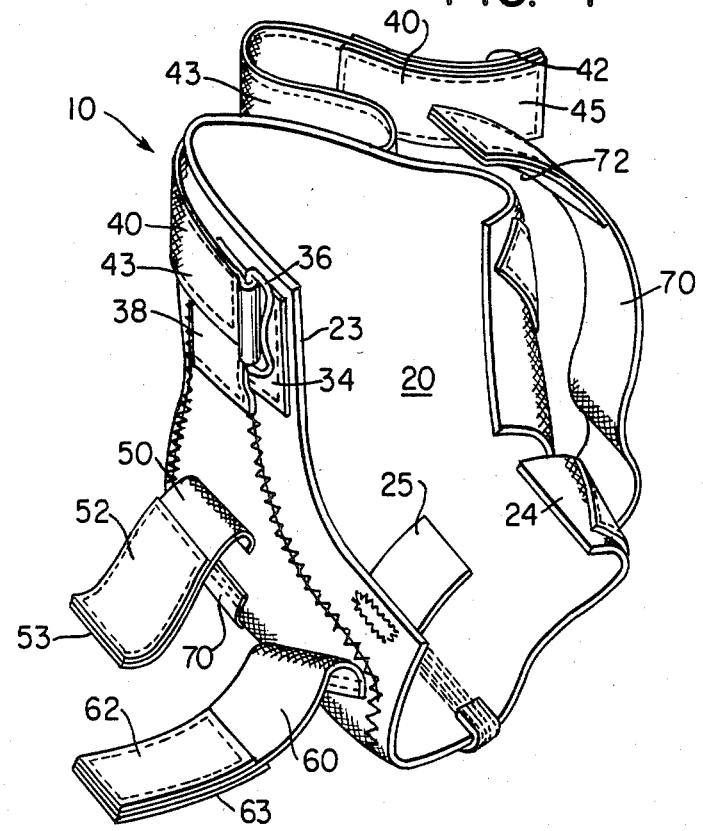

ANKLE SUPPORT

The present invention relates generally to ankle braces and, more particularly, concerns an ankle support which is fully adjustable to a wide range of sizes, for providing compression and firm support for the joint and ligaments of the ankle, without affecting their normal function.

BACKGROUND OF THE INVENTION

Traditionally, adhesive tape, or the like, has been applied to an injured or weakened ankle, in order to support the joint and ligaments thereof during physical activity. Although taping could lend significant support to the ankle, a substantial amount of time and effort is required in order to apply the tape properly, and the perspiration and rigors of physical activity can result in the loss of a significant proportion of the support after less than twenty minutes of use. Furthermore, after tape has been applied to the ankle of an athlete and he has had an opportunity to warm-up for several minutes, he may experience cramping, pinching or some other form of discomfort in one or more areas of the foot. To relieve this discomfort, little cuts are made in the tape in the areas of discomfort, in an effort to loosen the tape locally. However, each time such a cut is made, some of the strength of the tape is lost, and an early loss of the effectiveness of the entire structure becomes more likely.

In an effort to overcome some of the shortcomings of taping, use has been made of ankle braces. A typical prior art brace takes the form of a sheathe or stocking which is worn on the foot and lower leg. Some braces have made provision for selective tightening and adjustability, for example by means of laces. One shortcoming of such ankle braces is that they do not provide effective support to the lateral ligaments in the ankle, and to get any support, they must be secured so tightly that pinching and interruption of dorsal flexion occur. Securing the brace as tightly as needed for any meaningful support therefore would interfere with normal movement.

Another type of known ankle brace is a lace-up model with an elastic strap that fits over and around the ankle to provide elastic support for the ankle. The problem with elastic straps and the like is that they provide compression but very little support.

Other braces in use today, have little pockets that receive metal stays. They are used primarily for acute injuries, because they limit normal motions of the foot to an extreme degree and, if worn on a continued basis, can produce atrophy of the musculature in the region.

Broadly, it is an object of the present invention to overcome the disadvantages associated with ankle taping and prior ankle supports. It is a specific object to provide an ankle support which may be quickly and easily applied to and adjusted upon the wearer's leg, while offering a high degree of firm, inelastic support for the ankle joint, and not interfering with normal movement and use of the joint.

It is another object of the present invention to provide an ankle brace with a selectable amount of compression, in order to accommodate the swelling and soreness associated with ankle injuries.

It is yet another object of the present invention to provide an ankle brace with a high degree of adjustability, in order to accommodate a wide range of sizes and shapes of legs and feet.

It is a further object of the present invention to provide an ankle support which, when applied, does not change the shoe size of the wearer's foot and may be worn comfortably inside the shoe.

It is also an object of the present invention to provide and ankle support which is convenient, efficient and effective in use, yet relatively simple and inexpensive in construction.

In accordance with the present invention, an ankle support is provided with an underliner having multi-directional stretch which fits over the wearer's foot in the manner of a sock and extends to a point above the ankle. A non-stretch lateral strap is secured to the underliner at a point below the ankle joint and extends upwardly to the top of the underliner, where it is inelastically secured, with provision being made for adjustment of its tension. A non-stretch medial strap is inelastically connected to the lateral strap therebelow. The medial strap extends underneath the foot and up the opposite side thereof, and it is inelastically secured to the leg near the top of the underliner, with provision being made for adjustment of its tension. The medial strap thereby supports the wearer's arch and, in combination with the lateral strap, supports the ligaments of the ankle joint and provides a "heel lock", to limit and balance the lateral movement of the ankle joint.

In a preferred embodiment, the underliner is provided with hook and pile closures which permit adjustment of its fit and the compression it provides. A second lateral strap is inelastically connected to the first lateral and medial straps near the location of the base of the fifth metatarsil. This second lateral strap extends upwardly and is inelastically secured to the leg near the top of the underliner with provision being made for adjustment of tension. The inelastic securement (and adjustable tension) of all straps near the top of the underliner is provided by means of a non-stretch anchor strap which extends about the leg near the top of the underliner. The first and second lateral straps and the medial strap are secured at their tops to the anchor strap by means of hook and pile fasteners, and the medial strap wraps around the front of the ankle and over the first and second lateral straps, to aid in their securement. The hook and pile fasteners assure convenient and rapid adjustment of the ankle support.

BRIEF DESCRIPTION OF THE DRAWING

The foregoing brief description, as well as further objects, features, and advantages of the present invention will be more completely understood from the following detailed description of a presently preferred, but nonetheless illustrative, embodiment of the present invention, with reference being had to the accompanying drawings in which:

FIG. 1 is a perspective review showing an ankle support in accordance with the present invention in its applied position on the leg of a wearer;

FIG. 2 is a left side elevational view of the ankle support as shown in FIG. 1;

FIG. 3 is a front view of the ankle support;

FIG. 4 is a right side elevational view of the ankle support as shown in FIG. 1;

FIG. 5 is a rear view of the ankle support;

FIG. 6 is a top view of the ankle support; and

FIG. 7 is a perspective view of the ankle support in its open position, showing further details of various components.

DETAILED DESCRIPTION

Turning now to the details of the drawing, FIGS. 1-6 illustrate an ankle support embodying the present invention, as applied to the right leg of a wearer. The support 10 would be provided in an opposite version (a mirror image of the version illustrated) for use on the left leg, and in several sizes (e.g., small, medium and large) of each version. As will be explained more fully below, after application, the support 10 remains in the position shown and will readily fit inside the wearer's athletic shoes. Adjustments can be made quickly and easily, and usually, without removing the shoe.

The main body of ankle support 10 is an underliner 20, which is made of neoprene. A closed-celled rubber is used because it will not retain bacteria, fungi or other organisms that could propagate. The underliner has a multidirectional stretch and provides warmth and compression for the wearer's ankle. The underliner is unique in that it has a heel cut-out 21, which allows the brace to fit into an athletic shoe or any shoe without affecting the lengthwise fit of the shoe. The widthwise fit of most shoes is adjustable, for example by adjusting laces or wearing a sock of a different thickness, but lengthwise fit is normally more difficult, if not impossible, to adjust.

Ankle support 10 is somewhat unique in that it receives the wearer's foot from the front and is a front closing brace. It is closed by means of two components called the tibia or the calf closure device (22,23) and the dorsal closure device (24, 25), which is below the bone of the ankle. The numerals 22, 23 indicate a conventional hook and pile closure device, the hook and pile elements being indicated as 22 and 23, respectively. By adjusting the angle of hook element 22 and its overlap relationship to pile 23, the fit of the upper portion of the neoprene underliner is readily adjusted to accommodate a wide range of ankle and calf thicknesses.

The lower or dorsal portion of the underliner similarly includes a hook and a pile closure device 24, 25. The brace components are preferably secured to the underliner by stitching. The dorsal section again provides stretch and is applied by stretching the hook component 24 over the underliner and affixing the closure device 24, 25.

The combination of the adjustable upper and lower closure devices provides a very wide range of fit for many foot types. For example, the adjustment of the two closure devices relative to each other accommodates a wearer with a very thick or very wide lower leg and a thin or wide foot, and it provides for many other variations of calf size in relationship to foot size. It also does not interfere with normal dorsiflexion or plantarflexion of the ankle joint. Also, application of the underliner and adjusting the fit in the manner described above results in proper alignment of the other components of the brace to provide a more comfortable and more correct fit. The amount of compression of the underliner can, likewise, be adjusted in this manner.

The underliner of the present ankle support therefore provides a frontloading closure system, provides for a wide range of fit by having a tibia closure and a dorsal closure, and also provides an adjustable compression from the brace, as well as serving to align the other components of the brace.

A nylon stirrup member 30 that is affixed to the underliner so as to extend along either side of the leg and around the bottom of the foot in the fashion of a stirrup. Stirrup member 30 is preferably made of non-stretch nylon and is preferably secured by sewing. Stirrup 30 is formed in an "L-shaped" configuration on either side of the ankle, to provide a means for attaching the other components so that they will not stretch, whereby the brace, in which the various straps do not stretch, provides non-stretch support, not elastic support.

An anchor strap 40 forms a loop going all the way around the brace and all the way around the leg above the ankle. As will be explained more fully below, anchor strap 40 is constructed so that some of the other components of the brace can be anchored to it. To apply anchor strap 40, its end is inserted through a buckle 36 and the strap is pulled tight and folded back on itself. A piece of vinyl 34 is provided to protect the leg from the buckle 36. The outer surface of strap 40 is covered with a pile component 43 of a hook and pile closure device, and attached to the end of strap 40 is a piece of hook element 42. This piece of hook material 42 affixes to the pile 43 in order to secure another strap 40, and it creates an anchoring for stirrup 30. It also will anchor in place some of the other components. By using the hook and pile closure system for the anchor strap 40, it becomes an adjustable means of pressure or an adjustable means of tightness for the brace, so that it can also accommodate a wide range of lower leg sizes, yet it will encircle the leg and attach to itself. If the lower leg were very narrow, the hook component 42 could continue around the leg and attach to any portion of pile component 43.

A piece of pile component 38 is secured on the stirrup over the under-liner 20 below strap 40 so that first and second lateral straps 50 and 60 can be affixed with a little more security and with a little more bond to the brace. Both of these lateral straps (50 and 60) correlate to some of the ligaments of the ankle that are principally involved in an inversion or a lateral ligament sprain of the ankle. The ligaments that they correlate to are the anterior talofibular ligament (strap 60) and the calcaneo fibular ligament (strap 50), either or both of which might be stretched or partially or fully torn when an ankle sprain occurs.

The lateral strap 50, which will also be referred to as the calcaneus strap, correlates to the calcaneus or the heel bone of the foot. Pulling this non-stretch strap—the fact that it is non-stretch is very important—affects the calcaneus bone in such a manner that it closes the ankle joint (i.e., it effects the same mechanics on the joint that the ligaments will effect), so the strap supports or replaces those ligaments in the ankle. At its bottom, strap 50 is secured to stirrup member 30, preferably by sewing and it is secured at its top by means of a hook and pile closure system, of which the hook component 52 is on the rear of the strap 50 and affixes to pile components 40 and 38 by simply being pressed against them.

On the outside of Strap 50, there is a piece of pile component 53, to which strap 60 affixes by means of a hook component 62 on the rear of strap 60. Strap 60 is secured to stirrup 30 at a point corresponding to the base of the fifth metatarsal, to provide additional reinforcement to this ligament group of the ankle. The reason that the straps 50 and 60 are provided rather than only one strap is that the two straps offer a wider range of adjustment and accommodate a wider range of foot sizes, since it is possible to adjust independently of each other the straps 50 and 60 and their effect, comfort, positioning and fit.

A medial strap 70 is secured to stirrup 30 below and in general lengthwise alignment with strap 50, in order to gain the effect of a continuous strap. Strap 70 is also secured to the stirrup 30 so that its secured end is in general alignment with the secured end of strap 60. Strap 70 balances out the force that straps 50 and 60 have on the heel and on the subtalar joint, as well as on the positioning of the calcaneus of the heel bone. Adjusting the pulling relationship of the straps 50 and 70 with respect to each other provides what is commonly called a "heel lock" in which the foot is cradled, and lateral movement of the ankle joint is limited, balanced and aligned. Strap 70 extends under the foot, upwardly along the inside surface of the foot and across the front of the ankle. As strap 70 is pulled upward, it provides an antipronational force, which prevents rolling-in of the foot, and it provides support to the arch which is very important in taping, strapping or supporting the ankle. If straps 50 and 60 were pulled up too much and there were no support on the inside surface of the foot, the mechanism of the foot would be forced into a predisposition to pronate (rotation of the arch inwardly and down), but strap 70 counterbalances this effect on the subtalar joint and creates a heel lock.

Strap 70 continues across the outside surface of the leg and, by means of a hook element 72 of a hook and pile closure, is secured to the pile surface 43 on strap 40. As a result, it provides pressure on the hook and pile closures of straps 50 and 60, thereby holding those straps in place and keeping them from being torn off or loosened during use.

At the end of the anchor strap 40 there is a piece of pile component 45 on the outside. This provides a greater range of adjustment so as to accommodate a wide or narrow lower leg, a very thick or fat ankle or bone structure or a combination of bone and soft tissue. In order to increase the range of fit even further, a piece of pile component 63 is provided at the top and at the outside of strap 60. Hence, when strap 70 is wrapped around the foot, it may be secured to a portion of pile, no matter where hook element is positioned. Also, the way the material of the strap 72 contours to the foot, it will not interfere with dorsal flexion or plantar flexion of the ankle.

The brace is provided in a left version and a right version and, when applied, it is designed to resist lateral ligament sprains or inversion of the ankle joint without affecting plantarflexion or dorsiflexion of the ankle and/or to reduce instability to varus stress to the ankle. It provides support to the lateral ligaments of the ankle by means of two adjustable, non-stretchable straps which allow for comfort and adjustability of support, and it also provides a heel lock by means of the medial strap which provides a balancing affect on the ankle joint and provides support for the arch. The underliner provides compression, warmth, and adjustability.

When the present ankle support is in use, if the athlete feels that the brace is slipping down or loosening, he may adjust, tighten or loosen it in just seconds. Because the tightening of the support apparatus is above the shoe-line in most athletic shoes, it is very quick and simple to adjust. This type of adjustability and support has previously not been available in an ankle brace.

Although the present ankle support or brace is primarily designed to resist inversion sprains of the ankle, to reduce instability to varus stress and generally to provide warmth and compression to the ankle, it has been found useful for medial sprains or sprains that involve the deltoid ligament, which is on the inside of the ankle, by using the support on the wrong leg (e.g., a right leg support on the left ankle). The straps which should be on the outside of the ankle are then on the inside of the ankle and provide support to the medial, deltoid ligament which is frequently a site of injury.

Although a preferred embodiment of the invention has been disclosed for illustrative purposes, those skilled in the art will appreciate that many additions, modifications and substitutions are possible, without departing from the scope and spirit of the invention as defined by the accompanying claims.

What is claimed is:

1. An ankle support comprising:
    an underliner defining a main body for said support, said underliner being made of a stretchable material and fitting over a wearer's foot in the manner of a sock, and extending to a point above the wearer's ankle.
    a non-stretch lateral strap secured to the exterior surface of the underliner at a point between the bottom of the foot and the ankle joint and extending upwardly and in general alignment with the fibular ligament at the side of the foot to a point above the ankle joint, said strap being inelastically secured with respect to said leg at a point above said ankle joint so that the tension thereof may be selectively adjusted; and
    a non-stretch medial strap secured to the same side surface of the underliner as the lateral strap, extending under the arch of the foot and upwardly on the opposite side thereof, inelastically secured to the lateral strap and inelastically secured with respect to said leg at a point above the ankle joint so that the tension thereof may be selectively adjusted;
    said medial strap being effective to support the arch of the foot and, in combination with said lateral strap, supporting the ligaments of the ankle joint, thus limiting and balancing the lateral movement of the joint.

2. An ankle support in accordance with claim 1 wherein said underliner includes a cut-out at the rear thereof through which the rear of the wearer's heel may protrude, whereby the ankle support may be worn on a leg inside a shoe, without affecting the lengthwise fit of the shoe.

3. An ankle brace in accordance with claim 1 wherein said underliner is open at the front thereof and further includes upper and lower closure means, each constructed to permit adjustable securement of said underliner, whereby the fit and compression thereof may be selectively adjusted.

4. An ankle support in accordance with claim 3 wherein at least one of said closure means comprises a hook component and a complimentary pile component.

5. An ankle support in accordance with claim 1 further comprising a further non-stretch lateral strap inelastically connected to the first lateral strap and the medial strap and disposed at a point on said underliner in general alignment with the base of the fifth metatarsal of the foot, said further lateral strap extending upwardly and being inelastically secured with respect to said leg at a point above the ankle joint so that the tension thereof may be selectively adjusted.

6. An ankle support in accordance with claim 1 further comprising a non-stretch anchor strap inelastically secured with respect to said underliner so as to extend about the leg at a point above the ankle joint, the securement of at least one of said lateral strap and said medial strap with respect to said leg being achieved by means for detachably securing said one strap to said anchor strap.

7. An ankle support in accordance with claim 6 wherein the outwardly facing surface of said anchor strap includes one component of a hook and pile closure device, said lateral straps and said medial strap including the complimentary component of a hook and pile closure device on the inwardly facing surfaces thereof.

8. An ankle support in accordance with claim 7 wherein the outwardly facing surfaces of said lateral straps include said one component of a hook and pile closure device.

9. An ankle support in accordance with claim 8 wherein said medial strap extends over at least one of said lateral straps in contact therewith, whereby said medial strap aids in maintaining said lateral strap in secured relationship with respect to said leg.

10. An apparatus in accordance with claim 6 wherein the selective tension adjustment of at least one of said straps is provided by means of hook and pile closure means.

11. An ankle support in accordance with claim 6 wherein said medial strap extends across the front of said ankle and is secured with respect to said leg on the same side thereof as said first lateral strap.

12. An ankle support in accordance with claim 6 further comprising a non-stretch stirrup member secured over said underliner so as to extend under said foot and upwardly on either side of said leg, said lateral straps and said medial strap being inelastically secured to said stirrup member.

13. An ankle support in accordance with claim 12 wherein said stirrup member is L-shaped so as to extend along the lateral and medial margins of the foot.

14. An ankle support in accordance with claim 6 further comprising a further non-stretch lateral strap inelastically connected to the first lateral strap and the medial strap and disposed at a point on said underliner in general alignment with the base of the fifth metatarsal of the foot, said further lateral strap extending upwardly and being inelastically secured with respect to said leg at a point above the ankle joint so that the tension thereof may be selectively adjusted.

15. An apparatus in accordance with claim 14 wherein the selective tension adjustment of at least one of said straps is provided by means of hook and pile closure means.

16. An ankle support in accordance with claim 14 wherein the outwardly facing surface of said anchor strap includes one component of a hook and pile closure device, said lateral straps and said medial strap including the complimentary component of a hook and pile closure device on the inwardly facing surfaces thereof.

17. An ankle support in accordance with claim 16 wherein the outwardly facing surfaces of said lateral straps include said one component of a hook and pile closure device.

18. An ankle support in accordance with claim 17 wherein said medial strap extends over at least one of said lateral straps in contact therewith, whereby said medial strap aids in maintaining said lateral strap in secured relationship with respect to said leg.

19. An apparatus in accordance with claim 1 wherein the selective tension adjustment of at least one of said straps is provided by means of hook and pile closure means.

20. An ankle support in accordance with claim 1 wherein said medial strap extends across the front of said ankle and is secured with respect to said leg on the same side thereof as said first lateral strap.

21. An ankle support in accordance with claim 1 wherein the outwardly facing surface of said anchor strap includes one component of a hook and pile closure device, said lateral straps and said medial strap including the complimentary component of a hook and pile closure device on the inwardly facing surfaces thereof.

22. An ankle support in accordance with claim 21 wherein the outwardly facing surfaces of said lateral straps include said one component of a hook and pile closure device.

23. An ankle support in accordance with claim 22 wherein said medial strap extends over at least one of said lateral straps in contact therewith, whereby said medial strap aids in maintaining said lateral strap in secured relationship with respect to said leg.

24. An ankle support in accordance with claim 1 further comprising a non-stretch stirrup member secured over said underliner so as to extend under said foot and upwardly on either side of said leg, said lateral straps and said medial strap being inelastically secured to said stirrup member.

25. An ankle support in accordance with claim 24 wherein said stirrup member is L-shaped so as to extend along the lateral and medial margins of the foot.

* * * * *